(12) United States Patent
Tanaka et al.

(10) Patent No.: US 7,615,650 B2
(45) Date of Patent: Nov. 10, 2009

(54) PROCESS FOR PRODUCING CHROMAN COMPOUND

(75) Inventors: Kazuo Tanaka, Niitaga (JP); Youichi Kyuuko, Niigata (JP); Toshio Hidaka, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 558 days.

(21) Appl. No.: 10/587,545

(22) PCT Filed: Jan. 28, 2005

(86) PCT No.: PCT/JP2005/001263

§ 371 (c)(1),
(2), (4) Date: Jul. 28, 2006

(87) PCT Pub. No.: WO2005/073212

PCT Pub. Date: Aug. 11, 2005

(65) Prior Publication Data

US 2007/0179304 A1    Aug. 2, 2007

(30) Foreign Application Priority Data

Jan. 30, 2004    (JP) .............................. 2004-024126

(51) Int. Cl.
*C07D 311/66*    (2006.01)
(52) U.S. Cl. ..................... 549/405; 549/407; 549/408
(58) Field of Classification Search ................. 549/405, 549/407, 408
See application file for complete search history.

(56) References Cited

FOREIGN PATENT DOCUMENTS

| EP | 0 645 383 | 3/1995 |
|---|---|---|
| EP | 0 891 974 | 1/1999 |
| JP | 60-092283 | 5/1985 |
| JP | 2003-146981 | 5/2003 |
| WO | WO 01/92249 | 12/2001 |

OTHER PUBLICATIONS

Giancarlo Cravotto, et al., The Reactivity of 4-Hydroxycoumarin under Heterogeneous High-Intensity Sonochemical Conditions, Synthesis 2003, No. 8, pp. 1286-1291.
Supplementary European Search Report dated Feb. 16, 2009, for Application No. EP 05 70 4261.

*Primary Examiner*—Bernard Dentz
(74) *Attorney, Agent, or Firm*—Antonelli, Terry, Stout & Kraus, LLP.

(57) ABSTRACT

The invention provides a process for producing a chroman compound represented by formula (1), characterized in that the process includes allowing a phenol, an unsaturated compound, and a formaldehyde to react in the absence of catalyst and in the presence of water in an amount by mole 1 to 10 times that of the phenol.

According to the present invention, a high-purity chroman compound can be produced in the absence of catalyst and under mild conditions. In addition, the invention provides an industrial means for producing the compound, without using a large amount of an acid or a base serving as a reaction promoter or a catalyst, which would otherwise cause side reactions, apparatus corrosion, etc.

11 Claims, 1 Drawing Sheet

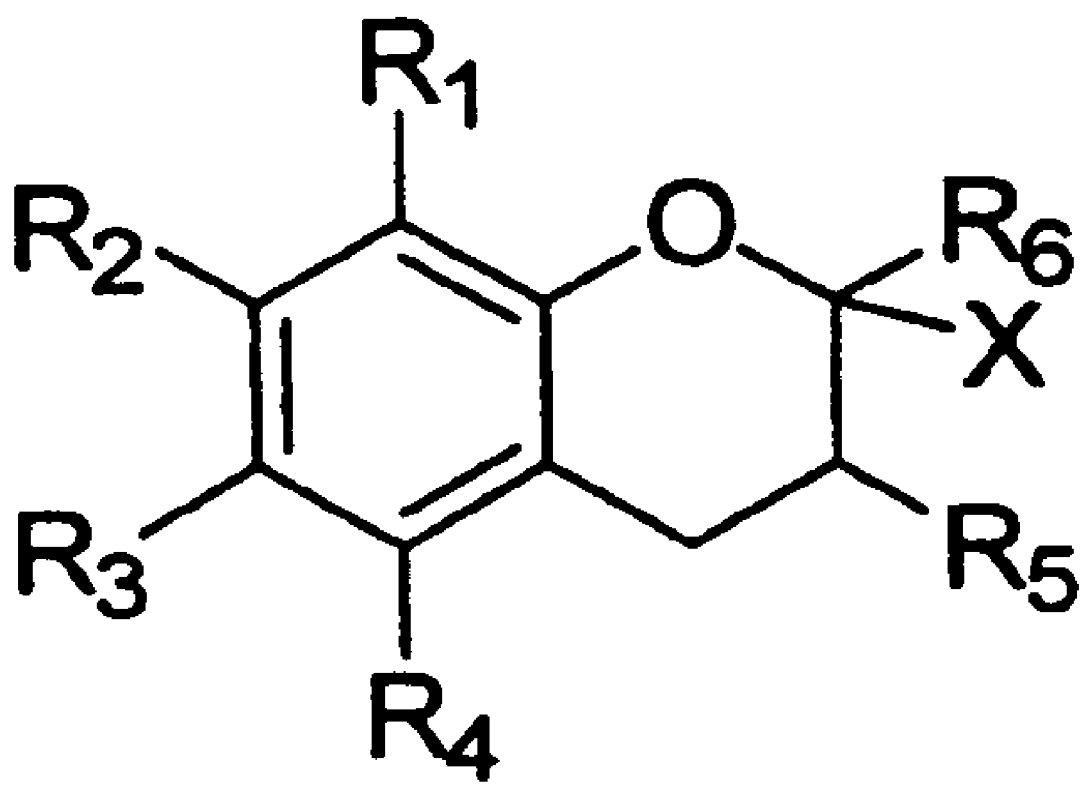

PROCESS FOR PRODUCING CHROMAN COMPOUND

TECHNICAL FIELD

The present invention relates to a process for producing a chroman compound and, more particularly, to an improved process for producing chromancarboxylic acid derivatives such as 6-hydroxy-2,5,7,8-tetramethylchroman-2-carboxylic acid and an ester thereof. The chromancarboxylic acid derivatives are important sources for drugs, vitamins, etc.

BACKGROUND ART

Heretofore, many methods for producing a chroman compound such as chromancarboxylic acid have been disclosed. For example, disclosed are a multi-step method employing starting materials including a phenol and an unsaturated carbonyl compound (see, for example, Patent Document 1); a method in which a phenol, a formaldehyde, and an unsaturated compound are allowed to react at 160 to 250° C. in hydrocarbon or halogenated aromatic hydrocarbon serving as a solvent (see, for example, Patent Document 2); a method in which a phenol, a formaldehyde, and an unsaturated compound are allowed to react in the presence of a secondary amine or an acid (see, for example, Patent Document 3); a two-step method (improved method of those disclosed in Patent Documents 2 and 3) including allowing a phenol, a formaldehyde, and an alcohol to react in the presence of an acid or a secondary amine, removing the secondary amine to the outside of the reaction system, and reacting the mixture with an unsaturated compound (see, for example, Patent Document 4); and a method in which a phenol, a formaldehyde, and an unsaturated compound are allowed to react in the presence of an acid (see, for example, Patent Document 5).

The method disclosed in Patent Document 1 requires many reaction steps for producing a target compound, and the time and the number of the steps should be reduced. Thus, the method is not suited for industrial production. The method disclosed in Patent Document 2 is a single-step process employing no catalyst, through which a chroman compound can be produced in a simple manner. However, the method for producing chromancarboxylic acid or a chromancarboxylic acid ester attains insufficient target yield. The method disclosed in Patent Document 3 employs an acid or an amine serving as a catalyst so as to enhance the product yield that has been attained through the method of Patent Document 2. However, when the target is chromancarboxylic acid, the target yield is poor, and large amounts of by-products are formed. In the method disclosed in Patent Document 4, reaction is carried out in two separate steps. Therefore, the method is cumbersome due to additional steps such as removal of catalyst. The method disclosed in Patent Document 5 produces a chromancarboxylic acid ester in the presence of acid. Although the method improves the yield of a chromancarboxylic acid ester to 60%, the yield is still insufficient, raising demand for further improvement.

In the methods disclosed in Patent Documents 2, 4, and 5, an acid serving as a catalyst is added in a considerably large amount; i.e., an amount of about 0.5 equivalents with respect to a phenol serving as a substrate, in an attempt to enhance rate of reaction and selectivity. As a result, apparatuses employed in the methods are corroded by a large amount of acid at high temperature, and complicated countermeasures must be taken for the apparatuses. Thus, these methods raise further problems to be solved for carrying out the method on an industrial scale.

As described hereinabove, each of these methods for synthesizing a chroman compound has both merits and demerits and still has problems when applied on an industrial scale.

Particularly when the target is a drug or health food, a high-purity compound must be produced at the lowest possible cost. Heretofore, through a conventional technique, high-purity chroman compounds, particularly chromancarboxylic acid derivatives, cannot be produced at high yield in simple operational steps on an industrial scale.

Patent Document 1: U.S. Pat. No. 4,026,907

Patent Document 2: Japanese Patent Application Laid-Open (kokai) No. 60-92283

Patent Document 3: Japanese Patent Application Laid-Open (kokai) No. 7-97380

Patent Document 4: Japanese Patent Application Laid-Open (kokai) No. 11-80147

Patent Document 5: Japanese Patent Application Laid-Open (kokai) No. 2003-146981

BRIEF DESCRIPTION OF THE DRAWING

The Drawing represents the product that is produced by the instant process.

DISCLOSURE OF THE INVENTION

An object of the present invention is to provide a process for producing a chroman compound, particularly a chromancarboxylic acid derivative, which method attains high product yield, is carried out in simple steps, does not cause damage such as corrosion of apparatuses, and can be readily carried out on an industrial scale.

The present inventors have carried out extensive studies in order to attain the aforementioned object, and have found that, when a phenol, a formaldehyde, and an unsaturated compound are allowed to react in the absence of catalyst but in the presence of a predetermined amount of water, reaction proceeds under conditions milder than those employed in a conventional method, whereby a chromancarboxylic acid ester and other compounds can be produced at high yield. Through employment of the above method, no acid serving as a catalyst for accelerating reaction is needed. In addition, corrosion of apparatuses by acid and other problems involved in conventional techniques can be solved, and side reactions are suppressed, whereby a high-purity target product can be obtained. The present invention has been accomplished on the basis of this finding.

Specifically, when 1,4-dihydroxy-2,3,5-trimethylbenzene, formaldehyde, and a methacrylate ester are used as reaction substrates in excessive amounts, and the mixture is allowed to react in the absence of solvent and catalyst but in the presence of water at 160° C., a chromancarboxylic acid ester of interest is formed at a yield as high as about 90%, which is higher than that obtained through a conventional technique, in accordance with the following reaction scheme.

[F1]

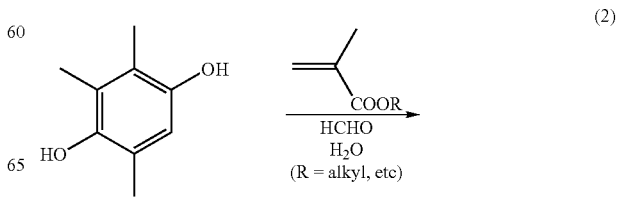

(2)

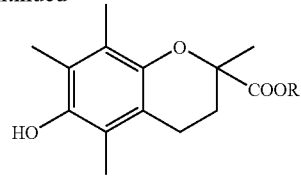

The aforementioned Patent Documents disclose conventional techniques in which a phenol, a formaldehyde, and an unsaturated compound are subjected to condensation, to thereby produce a chroman compound. However, these documents never disclose that reaction rate is surprisingly enhanced by intentional addition of water to the reaction system in the absence or presence of catalyst, whereby a target compound can be produced at high yield without using an acid which would otherwise causes corrosion or other damage of apparatuses.

The aforementioned Japanese Patent Application Laid-Open (kokai) No. 60-92283 (Patent Document 2) discloses a method for producing a chroman compound in which reaction is carried out in a hydrocarbon solvent in the absence of catalyst. The Patent Document discloses that water forms as the reaction proceeds, and since the thus-formed water is be co-boiled with reaction solvent, it may be removed through distillation in accordance with needs. In fact, in the Examples section of this Patent Document, water formed during condensation reaction was removed several times together with xylene vapor through distillation. Japanese Patent Application Laid-Open (kokai) No. 7-97380 (Patent Document 3) merely discloses that reaction is carried out in the presence of a secondary amine and an acid, which is an essential reaction condition, and never describes the effect of water. In Japanese Patent Application Laid-Open (kokai) No. 2003-146981 (Patent Document 5), however, use of a low-water-content formaldehyde polymer such as paraformaldehyde or trioxane is recommended. As mentioned above, none of the above documents disclosing conventional methods never discloses that a chromancarboxylic acid can be produced at high yield in the presence of water under mild conditions; i.e., absence of solvent and catalyst. Therefore, those skilled in the art never conceive the effect of water, and the process of the present invention is completely different from conventional techniques.

Accordingly, the present invention is directed to the following.

1. A process for producing a chroman compound represented by formula (1):

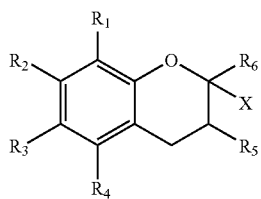

[F2]

(wherein each of substituents $R_1$ to $R_4$ represents a hydrogen atom, a halogen atom, a hydroxyl group, a methoxy group, an ethoxy group, a carboxyl group, a C1 to C12 alkyl group which may have a substituent, a C6 to C12 aryl group which may have a substituent, a C7 to C12 aralkyl group which may have a substituent; $R_1$ to $R_4$ may be linked to one another; each of $R_5$ to $R_6$ represents a hydrogen atom or a C1 to C12 alkyl group, and X represents a hydrogen atom, a carboxyl group, an amide group, a nitrile group, an aldehyde group, an ester group and a C1 to C12 alkyl group which may have a substituent, the substituent represents a halogen atom, a hydroxyl group, a carboxyl group or an ester group, characterized in that the process comprises allowing a phenol characterized in that the process comprises allowing a phenol represented by formula (2):

[F3]

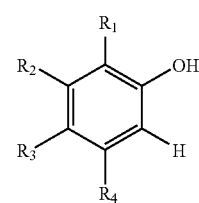

(wherein each of $R_1$ to $R_4$ represents as same as those of formula (1)), an unsaturated compound represented by formula (3):

[F4]

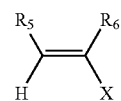

(wherein $R_5$, $R_6$ and X represents as same as those of formula (1)), and a formaldehyde to react in the absence of catalyst and in the presence of water in an amount by mole 1 to 10 times that of the phenol.

2. A process for producing a chroman compound as described in 1, wherein the phenol is an alkylphenol or a polyhydroxybenzene, and the unsaturated compound is at least one member selected from C3 to C24 aliphatic compounds.

3. A process for producing a chroman compound as described in 2, wherein the phenol is at least one member selected from the group consisting of 2-methylphenol, 3-methylphenol, 4-methylphenol, 2,3-dimethylphenol, 2,4-dimethylphenol, 2,5-dimethylphenol, 3,4-dimethylphenol, 3,5-dimethylphenol, 2,3,4-trimethylphenol, 2,3,5-trimethylphenol, 2,4,5-trimethylphenol, 3,4,5-trimethylphenol, 2,3,4,5-tetramethylphenol, hydroquinone, 1,4-dihydroxy-2-methylbenzene, 1,4-dihydroxy-2,3-dimethylbenzene, 1,4-dihydroxy-2,5-dimethylbenzene, 1,4-dihydroxy-2,6-dimethylbenzene, and 1,4-dihydroxy-2,3,5-trimethylbenzene, and the unsaturated compound is at least one member selected from the group consisting of acrylic acid, methyl acrylate, ethyl acrylate, acrylonitrile, acrylamide, acrolein, methacrylic acid, methyl methacrylate, ethyl methacrylate, isopropyl methacrylate, n-butyl methacrylate, isobutyl methacrylate, 2-hydroxyethyl methacrylate, 2-methylacrylonitrile, 2-methylacrylamide, methacrolein, crotonic acid, methyl crotonate, ethyl crotonate, crotononitrile, crotonamide, crotonaldehyde, crotonalcohol, 2-methylcrotonic acid, methyl 2-methylcrotonate, ethyl 2-methylcrotonate, 2-methylcrotononitrile, 2-methylcrotonamide, 2-methylcrotonaldehyde, 2-methylcrotonalcohol, 3-methylcrotonic acid, methyl 3-methylcrotonate, ethyl 3-methylcrotonate, 3-methylcrotononitrile, 3-methylcrotonamide, 3-methylcrotonaldehyde, 3-methylcrotonalcohol, 4-methyl-pent-4-enoic acid, 4-methyl-pent-4-enoic acid methyl ester, 4-methyl-pent-4-enoic acid ethyl ester, 4-methyl-pent-4-enal, 4-methyl-pent-4-en-1-ol, 3-methyl-but-3-en-1-ol, and 2-methyl-prop-2-en-1-ol.

4. A process for producing a chromancarboxylic acid ester represented by formula (4):

[F5]

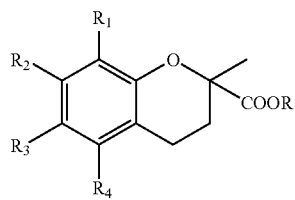

(4)

(wherein each of $R_1$ to $R_4$ represents a hydrogen atom, a halogen atom, a hydroxyl group, a methoxy group, an ethoxy group, a carboxyl group, or a C1 to C12 alkyl group which may have a substituent, a C6 to C12 aryl group which may have a substituent, a C7 to C12 aralkyl group which may have a substituent; $R_1$ to $R_4$ may be linked to one another; R represents a C1 to C12 alkyl group which may have a substituent, the substituent represents a halogen atom, a hydroxyl group, a carboxyl group or an ester group), the process including allowing a phenol represented by formula (2):

[F6]

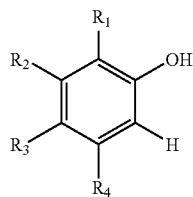

(2)

(wherein each of substituents $R_1$ to $R_4$ represents as same as those of formula (4)),

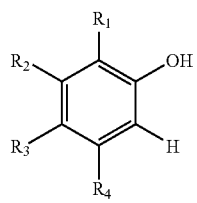

a methacrylate ester represented by formula (5):

[F7]

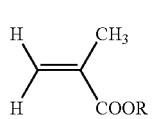

(5)

(wherein R represents as same as those of formula (4)), and a formaldehyde to react in the absence of catalyst and in the presence of water, wherein the amount of water caused to be present in the reaction system is 1 to 10 times by mole that of the phenol.

5. A process for producing a chromancarboxylic acid ester as described in 4, wherein the phenol is an alkylphenol or a polyhydroxybenzene.

6. A process for producing a chromancarboxylic acid ester as described in 5, wherein the phenol is at least one member selected from the group consisting of 2-methylphenol, 3-methylphenol, 4-methylphenol, 2,3-dimethylphenol, 2,4-dimethylphenol, 2,5-dimethylphenol, 3,4-dimethylphenol, 3,5-dimethylphenol, 2,3,4-trimethylphenol, 2,3,5-trimethylphenol, 2,4,5-trimethylphenol, 3,4,5-trimethylphenol, 2,3,4,5-tetramethylphenol, hydroquinone, 1,4-dihydroxy-2-methylbenzene, 1,4-dihydroxy-2,3-dimethylbenzene, 1,4-dihydroxy-2,5-dimethylbenzene, 1,4-dihydroxy-2,6-dimethylbenzene, and 1,4-dihydroxy-2,3,5-trimethylbenzene, and the methacrylate ester is at least one member selected from the group consisting of methyl methacrylate, ethyl methacrylate, isopropyl methacrylate, n-butyl methacrylate, isobutyl methacrylate, and 2-hydroxyethyl methacrylate.

7. A process for producing a chromancarboxylic acid ester according to 4, wherein the methacrylate ester and the formaldehyde are used in amounts in stoichiometrically excess of the amount of the phenol.

8. A process for producing a chromancarboxylic acid ester according to 4, wherein the formaldehyde is at least one member selected from the group consisting of formaldehyde and paraformaldehyde.

9. A process for producing methyl 6-hydroxy-2,5,7,8-tetramethylchroman-2-carboxylate, characterized in that the process comprises allowing 1,4-dihydroxy-2,3,5-trimethylbenzene, methyl methacrylate, and a formaldehyde to react in the absence of catalyst and in the presence of water in an amount by mole 1 to 10 times that of 1,4-dihydroxy-2,3,5-trimethybenzene.

10. A process for producing a chromancarboxylic acid, characterized by comprising hydrolyzing a chromancarboxylic acid ester produced through a process according to any of 4 to 8 or methyl 6-hydroxy-2,5,7,8-tetramethylchroman-2-carboxylate produced through a process according to claim 9.

According to the present invention, a high-purity chroman compound can be produced in the absence of catalyst and under mild conditions. In addition, the invention provides an industrial means for producing the compound, without using a large amount of an acid or a base serving as a reaction promoter or a catalyst, which would otherwise cause side reactions, apparatus corrosion, etc.

BEST MODES FOR CARRYING OUT THE INVENTION

Reaction substrates employed in the present invention are a phenol, a formaldehyde, and an unsaturated compound. The phenol can be represented by formula (2):

[F8]

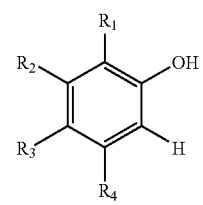

(wherein each of $R_1$ to $R_4$ represents a hydrogen atom, a halogen atom, a hydroxyl group, a methoxy group, an ethoxy group, a carboxyl group or a C1 to C12 alkyl group which may have a substituent, a C6 to C12 aryl group which may have a substituent, a C7 to C12 aralkyl group which may have a substituent; $R_1$ to $R_4$ may be linked to one another; the substituent represents a halogen atom, a hydroxyl group, a carboxyl group or an ester group.

Preferred phenols include alkylphenols and polyhydroxybenzenes. Specific examples of the phenol employed in the invention include 2-methylphenol, 3-methylphenol, 4-methylphenol, 2,3-dimethylphenol, 2,4-dimethylphenol, 2,5-dimethylphenol, 3,4-dimethylphenol, 3,5-dimethylphenol, 2,3,4-trimethylphenol, 2,3,5-trimethylphenol, 2,4,5-trimethylphenol, 3,4,5-trimethylphenol, 2,3,4,5-tetramethylphenol, hydroquinone, 1,4-dihydroxy-2-methylbenzene, 1,4-dihydroxy-2,3-dimethylbenzene, 1,4-dihydroxy-2,5-dimethylbenzene, 1,4-dihydroxy-2,6-dimethylbenzene, 1,4-dihydroxy-2,3,5-trimethylbenzene, 1-naphthol, 2-naphthol, 2-phenylphenol, 3-phenylphenol, 4-phenylphenol, 2-methyl-3-phenylphenol, 2-phenyl-4-methylphenol, 2-phenyl-5-methylphenol, 3-phenyl-4-methylphenol, 3-phenyl-5-methylphenol, 2-phenyl-3,4-dimethylphenol, 2-phenyl-3,5-dimethylphenol, 2-phenyl-4,5-dimethylphenol, 2-phenyl-3,4,5-trimethylphenol, 1,4-dihydroxy-2-phenylbenzene, 1,4-dihydroxy-2-phenyl-3-methylbenzene, 1,4-dihydroxy-2-phenyl-5-methylbenzene, 1,4-dihydroxy-2-phenyl-6-methylbenzene, 1,4-dihydroxy-2-phenyl-3,5-dimethylbenzene, and 4,4'-dihydroxybiphenyl.

Among them, particularly preferred are 2-methylphenol, 3-methylphenol, 4-methylphenol, 2,3-dimethylphenol, 2,4-dimethylphenol, 2,5-dimethylphenol, 3,4-dimethylphenol, 3,5-dimethylphenol, 2,3,4-trimethylphenol, 2,3,5-trimethylphenol, 2,4,5-trimethylphenol, 3,4,5-trimethylphenol, 2,3,4,5-tetramethylphenol, hydroquinone, 1,4-dihydroxy-2-methylbenzene, 1,4-dihydroxy-2,3-dimethylbenzene, 1,4-dihydroxy-2,5-dimethylbenzene, 1,4-dihydroxy-2,6-dimethylbenzene, and 1,4-dihydroxy-2,3,5-trimethylbenzene.

In the present invention, the aforementioned phenols may be employed singly or in combination of two or more species serving as reaction substrates.

As used herein, the term "a formaldehyde" includes formaldehyde, aqueous formaldehyde solution, or paraformaldehyde which can form formaldehyde or formaldehyde solution.

In the present invention, though any one may be used, aqueous formaldehyde solution and paraformaldehyde in the presence of water are preferably used.

The unsaturated compound which is used in the present invention can be represented by formula (3):

[F9]

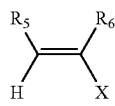

(wherein each of $R_5$ to $R_6$ represents a hydrogen atom or a C1 to C12 alkyl group, and X represents a hydrogen atom, a carboxyl group, an amide group, a nitrile group, an aldehyde group, an ester group and a C1 to C12 alkyl group which may have a substituent, the substituent represents a halogen atom, a hydroxyl group, a carboxyl group or an ester group)

Examples of the unsaturated compound employed in the present invention include compounds each having at least one carbon-carbon double bond in the structure thereof. Examples of preferred unsaturated compounds include C3 to C24 aliphatic compounds; e.g., acrylic acid, methyl acrylate, ethyl acrylate, acrylonitrile, acrylamide, acrolein, methacrylic acid, methyl methacrylate, ethyl methacrylate, isopropyl methacrylate, n-butyl methacrylate, isobutyl methacrylate, 2-hydroxyethyl methacrylate, 2-methylacrylonitrile, 2-methylacrylamide, methacrolein, crotonic acid, methyl crotonate, ethyl crotonate, crotononitrile, crotonamide, crotonaldehyde, crotonalcohol, 2-methylcrotonic acid, methyl 2-methylcrotonate, ethyl 2-methylcrotonate, 2-methylcrotononitrile, 2-methylcrotonamide, 2-methylcrotonaldehyde, 2-methylcrotonalcohol, 3-methylcrotonic acid, methyl 3-methylcrotonate, ethyl 3-methylcrotonate, 3-methylcrotononitrile, 3-methylcrotonamide, 3-methylcrotonaldehyde, 3-methylcrotonalcohol, 4-methyl-pent-4-enoic acid, 4-methyl-pent-4-enoic acid methyl ester, 4-methyl-pent-4-enoic acid ethyl ester, 4-methyl-pent-4-enal, 4-methyl-pent-4-en-1-ol, 3-methyl-but-3-en-1-ol, and 2-methyl-prop-2-en-1-ol. Of these, methacrylic acid esters such as methyl methacrylate, ethyl methacrylate, isopropyl methacrylate, n-butyl methacrylate, isobutyl methacrylate, and 2-hydroxyethyl methacrylate are particularly preferred.

The compounds which can be produced according to the present invention are represented by the following formula (1):

[F3]

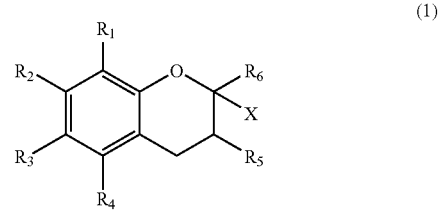

Each of $R_1$ to $R_4$ represents a hydrogen atom, a halogen atom, a hydroxyl group, a methoxy group, an ethoxy group, a carboxyl group or a C1 to C12 alkyl group which may have a substituent, a C6 to C12 aryl group which may have a substituent, a C7 to C12 aralkyl group which may have a substituent; $R_1$ to $R_4$ may be linked to one another.

Each of $R_5$ to $R_6$ represents a hydrogen atom or a C1 to C12 alkyl group, and X represents a hydrogen atom, a carboxyl group, an amide group, a nitrile group, an aldehyde group, an ester group and C1 to C12 alkyl group which may have a substituent.

Examples of the substituent connected to the aforementioned alkyl group, aryl group, or aralkyl group include a hydroxyl group, a halogen atom, a carboxyl group and an ester group.

Specific examples of the compound represented by formula (1) include 6-hydroxy-2,5,7-trimethyl-chroman-2-carboxylic acid, methyl 6-hydroxy-2,5,7-trimethyl-chroman-2-carboxylate, 6-hydroxy-2,5,8-trimethyl-chroman-2-carboxylic acid, methyl 6-hydroxy-2,5,8-trimethyl-chroman-2-carboxylate, 6-hydroxy-2,7,8-trimethyl-chroman-2-carboxylic acid, methyl 6-hydroxy-2,7,8-trimethyl-chroman-2-carboxylate, methyl 6-hydroxy-2,5,7-trimethyl-chroman-2-carboxylate, 6-hydroxy-2,5,7-trimethyl-2-methylcarboxymethylchroman, 6-hydroxy-2,5,7-trimethyl-2-hydroxymethylchroman, 6-hydroxy-2,5,7- trimethyl-2-hydroxyethylchroman, 6-hydroxy-2,5,7-trimethyl-2-carboxyethylchroman, 6-hydroxy-2,5,7-trimethyl-2-ethylcarboxyethylchroman, 6-hydroxy-2,5,7,8-tetramethylchroman-2-carboxylic acid, methyl 6-hydroxy-2,5,7,8-tetramethyl-chroman-2-carboxylate, 6-hydroxy-2,5,7,8-tetramethyl-2-methylcarboxymethylchroman, 6-hydroxy-2,5,7,8-tetramethyl-2-ethylcarboxymethylchroman, 6-hydroxy-2,5,7,8-tetramethyl-2-methylcarboxyethylchroman, 6-hydroxy-2,5,7,8-tetramethyl-chroman-2-carboxylic acid ethyl ester, 6-hydroxy-2,5,7,8-tetramethyl-2-cromanol, 2-(2-hydroxy-ethyl)-2,5,7,8-tetramethyl-chroman-6-ol, and 2-(2-hydroxy-methyl)-2,5,7,8-tetramethyl-chroman-6-ol. The process of the present invention is applicable to the production of these compounds.

The production process of the present invention is preferably applied to production of, among others, chromancarboxylic acid esters, which are compounds represented by formula (1) in which X is an ester group. Particularly, the process is preferably employed to produce 6-hydroxy-2,5,7,8-tetramethyl-chroman-2-carboxylic acid esters.

In the present invention, a phenol, a formaldehyde, and an unsaturated compound are caused to be reacted in the absence of catalyst and in the presence of water in an amount by mole 1 to 10 times that of the phenol. An acid or a base may be co-present in the reaction system, so long as the amount thereof is a catalytic amount and the effect of the invention is not impaired. In the case where water is caused to present, when an aqueous formaldehyde solution is employed, no additional water is needed. When paraformaldehyde is used instead of formaldehyde, water must be added.

In the process for producing a chroman compound of the present invention, reaction solvent is not necessarily used. When a solvent other than reaction substrates is present, the process operation becomes complicate. Thus, upon reaction, an unsaturated compound is preferably used in an excessive amount. For example, in the case where a combination of 1,4-dihydroxy-2,3,5-trimethylbenzene, an aqueous formaldehyde-solution, and methyl methacrylate is employed, when methyl methacrylate is used in an excessive amount, methyl methacrylate also serves as a reaction solvent.

The formaldehyde serving as a reaction substrate is preferably used in an amount excessive with respect to that of the phenol serving as a starting material. The amount of the formaldehyde may be predetermined so as to fall within a range of 1 to 20 mol with respect to 1 mol of starting phenol. The amount of the unsaturated compound is also preferably excessive, and may be predetermined so as to fall within a range of 1 to 10 mol, particularly preferably 1 to 5 mol, with respect to 1 mol of starting phenol. As described above, the amount of water is essentially 1 to 10 mol with respect to 1 mol of the phenol, more preferably 1 to 5 mol. When the amount of water is not appropriate, the yield of the product; i.e., a chroman compound such as a chromancarboxylic acid, decreases, whereas when the amount of water is less than 1 mol, addition of a phenol to formaldehyde occurring in the initial stage of reaction does not sufficiently proceed. In the latter case, a highly reactive unsaturated compound is prone to undergo side reaction at high temperature, decreasing the product yield.

When the amount of water is in excess of 10 mol, side reaction between water and an unsaturated compound cannot be negligible. As a result, the relative amount (by mole) of the unsaturated compound to that of the phenol decreases, leading to drop in product yield. Therefore, the amount of water preferably falls within the above range.

The reaction temperature is generally 80 to 250° C., preferably 100 to 230° C., particularly preferably 140 to 170° C. The reaction time, depending on the reaction temperature, is generally about 0.5 to about 10 hours, preferably 1 to 4 hours. However, a long reaction time does not cause any problems.

The reaction may be performed in any modes of a batch mode, a semi-batch mode, and a continuous mode. The mode may be appropriately selected in consideration of production scale or other factors.

The chromancarboxylic acid ester formed through the aforementioned reaction may be separated from the reaction mixture through a process, for example, a method in which the reaction mixture is cooled after completion of reaction, thereby precipitating crystals thereof, followed by filtration; or a workup process including concentration, extraction, and addition of solvent.

Generally, the product can be readily obtained by cooling to precipitate crystals, followed by filtration. In the case where methyl 6-hydroxy-2,5,7,8-tetramethylchroman-2-carboxylate is produced, trimethylhydroquinone, an aqueous formaldehyde, and methyl methacrylate are caused to react in the absence of catalyst, and the reaction product is cooled after completion of reaction. Subsequently, through merely addition of methanol to the reaction mixture, high-purity crystals of the product can be yielded.

The thus-produced chromancarboxylic acid ester is hydrolyzed, to thereby form the corresponding chromancarboxylic acid. This process also falls within the scope of the present invention. In a specific case, methyl 6-hydroxy-2,5,7,8-tetramethylchroman-2-carboxylate produced through the aforementioned process is hydrolyzed in a routine manner, whereby high-purity 6-hydroxy-2,5,7,8-tetramethylchroman-2-carboxylic acid, which has been very difficult to obtain through a conventional technique, can be produced in a simple process at high yield.

EXAMPLES

The present invention will next be described in more detail by way of Examples and Comparative Examples, which should not be construed as limiting the invention thereto.

Example 1

Methyl 6-hydroxy-2,5,7,8-tetramethyl-chroman-2-carboxylate

Into a 30-mL stainless-steel pressure reactor equipped with a stirrer, 1,4-dihydroxy-2,3,5-trimethylbenzene (1.0 g, 6.6 mmol), an aqueous formalin solution (1.1 g, formaldehyde 37 wt. %, methanol 7 wt. %, and water 56 wt. %), and methyl methacrylate (3.3 g, 32.9 mmol) were placed. The mixture was allowed to react at 180° C. for three hours under stirring, while the reactor was tightly closed. After completion of reaction, the reaction mixture was cooled to room temperature, and methanol was added to the mixture, whereby crystals were precipitated. The crystals were collected through filtration, to thereby yield methyl 6-hydroxy-2,5,7,8-tetramethyl-chroman-2-carboxylate in the form of white powder (1.45 g, 5.5 mmol). Reaction scores on the basis of 1,4-dihydroxy-2,3,5-trimethylbenzene and chemical purity which was determined through high-performance liquid chromatography (HPLC) were found to be as follows:

Percent conversion: 100%

Isolation yield: 83.3%

Chemical purity: 96%

Comparative Example 1

Methyl 6-hydroxy-2,5,7,8-tetramethyl-chroman-2-carboxylate

The procedure of Example 1 was repeated, except that acetic acid (0.2 g, 3.3 mmol) was further added to the mixture, to thereby yield a white powder (1.0 g, 3.8 mmol). Reaction scores on the basis of 1,4-dihydroxy-2,3,5-trimethylbenzene and chemical purity which was determined through HPLC were found to be as follows:
Percent conversion: 100%
Isolation yield: 57.4%
Chemical purity: 79%

Example 2

Methyl 6-hydroxy-2,5,7,8-tetramethyl-chroman-2-carboxylate

Into a 30-mL stainless-steel pressure reactor equipped with a stirrer, 1,4-dihydroxy-2,3,5-trimethylbenzene (1.0 g, 6.6. mmol), paraformaldehyde (0.4 g, 13.2 mmol), methyl methacrylate (3.3 g, 32.9 mmol), and water (0.29 g, 16.1 mmol) were placed. The mixture was allowed to react at 180° C. for three hours under stirring, while the reactor was tightly closed. After completion of reaction, the reaction mixture was cooled to room temperature, and methanol was added to the mixture, whereby crystals were precipitated. The crystals were collected through filtration, to thereby yield methyl 6-hydroxy-2,5,7,8-tetramethyl-chroman-2-carboxylate in the form of white powder (1.3 g, 4.9 mmol). Reaction scores on the basis of 1,4-dihydroxy-2,3,5-trimethylbenzene and chemical purity which was determined through HPLC were found to be as follows:
Percent conversion: 100%
Isolation yield: 74.2%
Chemical purity: 92.5%

Comparative Example 2

Methyl 6-hydroxy-2,5,7,8-tetramethylchroman-2-carboxylate

The procedure of Example 2 was repeated, except that the amount of water added was altered to be 0.06 g (3.3 mmol), to thereby yield methyl 6-hydroxy-2,5,7,8-tetramethylchroman-2-carboxylate in the form of white powder (1.1 g, 4.1 mmol). Reaction scores on the basis of 1,4-dihydroxy-2,3,5-trimethylbenzene and chemical purity which was determined through HPLC were found to be as follows:
Percent conversion: 75.0%
Isolation yield: 55.5%
Chemical purity: 85.5%

Comparative Example 3

Methyl 6-hydroxy-2,5,7,8-tetramethyl-chroman-2-carboxylate

The procedure of Example 2 was repeated, except that water was not added to the mixture, to thereby yield a white powder (0.6 g, 2.3 mmol). Reaction scores and chemical purity which was determined through HPLC were found to be as follows:
Percent conversion: 49%
Isolation yield: 34.8%
Chemical purity: 70.5%

Comparative Example 4

Methyl 6-hydroxy-2,5,7,8-tetramethyl-chroman-2-carboxylate

The procedure of Example 2 was repeated, except that no water was added but acetic acid (0.2 g, 3.3 mmol) was added. Reaction scores on the basis of 1,4-dihydroxy-2,3,5-trimethylbenzene were found to be as follows:
Percent conversion: 100%
Isolation yield: 60.6%
Chemical purity: 82.0%

Example 3

Methyl 6-hydroxy-2,7,8-trimethyl-chroman-2-carboxylate

Into a 30-mL stainless-steel pressure reactor equipped with a stirrer, 1,4-dihydroxy-2,3-dimethylbenzene (0.91 g, 6.6 mmol), an aqueous formalin solution (0.73 g, formaldehyde 37 wt. %, methanol 7 wt. %, and water 56 wt. %), and methyl methacrylate (8.3 g, 83.0 mmol) were placed. The mixture was allowed to react at 180° C. for three hours under stirring, while the reactor was tightly closed. After cooling, the reaction mixture was analyzed, and methyl 6-hydroxy-2,7,8-trimethylchroman-2-carboxylate was found to be formed as a chroman compound. Reaction scores on the basis of 1,4-dihydroxy-2,3-dimethylbenzene were found to be as follows:
Percent conversion: 89.1%
Isolation yield: 46.8%
Chemical purity: 94.1%

Example 4

Ethyl 6-hydroxy-2,5,7,8-tetramethyl-chroman-2-carboxylate

Into a 30-mL stainless-steel pressure reactor equipped with a stirrer, 1,4-dihydroxy-2,3,5-trimethylbenzene (1.0 g, 6.6 mmol), an aqueous formalin solution (1.3 g, formaldehyde 37 wt. %, methanol 7 wt. %, and water 56 wt. %), and ethyl methacrylate (6.59 g, 57.7 mmol) were placed. The mixture was allowed to react at 180° C. for four hours under stirring, while the reactor was tightly closed. After completion of reaction, the reaction mixture was cooled to room temperature. Through GC analysis, ethyl 6-hydroxy-2,5,7,8-tetramethylchroman-2-carboxylate was found to be formed. Reaction scores on the basis of 1,4-dihydroxy-2,3,5-trimethylbenzene were found to be as follows:
Percent conversion: 100%
Isolation yield: 32.3%
Chemical purity: 88.8%

Example 5

Production of methyl 6-hydroxy-5,7,8-trimethyl-chroman-2-carboxylate

Into a 30-mL stainless-steel pressure reactor equipped with a stirrer, 1,4-dihydroxy-2,3,5-trimethylbenzene (1.0 g, 6.6. mmol), an aqueous formalin solution (1.1 g, formaldehyde 37 wt. %, methanol 7 wt. %, and water 56 wt. %), and methacrylate (3.0 g, 34.3 mmol) were placed. The mixture was allowed to react at 180° C. for three hours under stirring, while the reactor was tightly closed. After completion of reaction, the reaction mixture was cooled to room temperature and analyzed through GC. Reaction scores on the basis of 1,4-dihydroxy-2,3,5-trimethylbenzene were found to be as follows:
Percent conversion: 100%
Isolation yield: 55.9%
Chemical purity: 87.0%

Example 6

Methyl 6-hydroxy-2,5,7,8-tetramethyl-chroman-2-carboxylate

Into a 1000-L stainless-steel pressure reactor, 1,4-dihydroxy-2,3,5-trimethylbenzene (100 kg), an aqueous formalin solution (107 kg, formaldehyde 37 wt. %, methanol 7 wt. %, and water 56 wt. %), and methyl methacrylate (395 kg) were placed. The mixture was allowed to react at 160° C. for four hours. During reaction, inner pressure of the reactor was 1.1 MPa.

After completion of reaction, the mixture was left to stand overnight so as to be cooled to room temperature. The reaction mixture was filtered, and the obtained solid was washed with methanol and dried by means of a conical dryer, to thereby yield methyl 6-hydroxy-2,5,7,8-tetramethylchroman-2-carboxylate (137.3 kg) in the form of white powder.

Reaction scores on the basis of 1,4-dihydroxy-2,3,5-trimethylbenzene and chemical purity which was determined through high-performance liquid chromatography (HPLC) were found to be as follows:
Percent conversion: 100%
Isolation yield: 80%
Chemical purity: 94.8%

Example 7

6-Hydroxy-2,5,7,8-tetramethyl-chroman-2-carboxylic acid

Into a 2000-L reactor provided with glass lining, methyl 6-hydroxy-2,5,7,8-tetramethyl-chroman-2-carboxylate (137.3 kg) obtained in Example 6 was placed and dissolved in methanol (137.3 kg). A solution containing water (411 kg) and sodium hydroxide (27 kg) was added dropwise thereto over two hours, whereby hydrolysis was performed at 80° C. for two hours. The hydrolyzed mixture was neutralized with a solution of potassium hydrogensulfate (91.9 kg) dissolved in water (411.9 kg) at 80° C. for two hours. The reaction mixture was centrifuged, and the obtained crystals were dried by means of a conical drier, to thereby yield 6-hydroxy-2,5,7,8-tetramethyl-chroman-2-carboxylic acid (130.2 kg) in the form of white powder. Reaction scores on the basis of 6-hydroxy-2,5,7,8-tetramethyl-chroman-2-carboxylate and chemical purity which was determined through high-performance liquid chromatography (HPLC) were found to be as follows:
Percent conversion: 99.9%
Isolation yield: 99.3%
Chemical purity: 99.6%

INDUSTRIAL APPLICABILITY

According to the process of the present invention in which a phenol, a formaldehyde, and an unsaturated compound are allowed to react in the absence of catalyst but in the presence of water in an amount by mole 1 to 10 times that of the phenol, reaction proceeds under the conditions milder than those employed in a conventional method. Thus, a high-purity chroman compound can be produced at high yield. In addition, since an acid serving as a catalyst for accelerating reaction is not used in the process, corrosion of apparatuses by acid and other problems involved in conventional techniques can be solved.

The invention claimed is:

1. A process for producing a chroman compound represented by formula (1):
[F1]

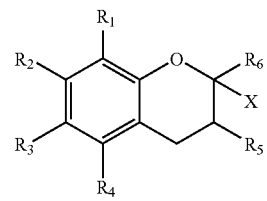

(1)

(wherein each of substituents $R_1$ to $R_4$ represents a hydrogen atom, a halogen atom, a hydroxyl group, a methoxy group, an ethoxy group, a carboxyl group, a C1 to C12 alkyl group which may have a substituent, a C6 to 012 aryl group which may have a substituent, a C7 to C12 aralkyl group which may have a substituent, or an ester residue; $R_1$ to $R_4$ may be linked to one another; each of $R_5$ to $R_6$ represents a hydrogen atom or a C1 to C12 alkyl group, and X represents a hydrogen atom, a carboxyl group, an amide group, a nitrile group, an aldehyde group, an ester group and a C1 to C12 alkyl group which may have a substituent, the substituent represents a halogen atom, a hydroxyl group, a carboxyl group or an ester group, characterized in that the process comprises allowing a phenol represented by formula (2):

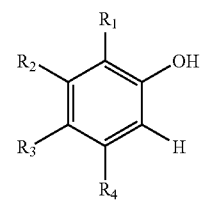

(2)

(wherein each of $R_1$ to $R_4$ represents as same as those of formula (1)), an unsaturated compound represented by formula (3):

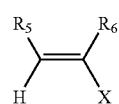

(3)

(wherein $R_5$, $R_6$ and X represent as same as those of formula (1)) and a formaldehyde to react in the absence of catalyst and in the presence of water in an amount by mole 1 to 10 times that of the phenol.

2. A process for producing a chroman compound as described in claim 1, wherein the phenol is an alkylphenol or a polyhydroxybenzene, and the unsaturated compound is at least one member selected from the group consisting of $C_3$ to $C_{24}$ aliphatic compounds.

3. A process for producing a chroman compound as described in claim 2, wherein the phenol is at least one member selected from the group consisting of 2-methylphenol, 3-methylphenol, 4-methylphenol, 2,3-dimethyl phenol, 2,4-dimethylphenol, 2,5-dimethylphenol, 3,4-dimethylphenol, 3,5-dimethylphenol, 2,3,4-trimethylphenol, 2,3,5-trimethylphenol, 2,4,5-trimethylphenol, 3,4,5-trimethyl phenol, 2,3,4,5-tetramethylphenol, hydroquinone, 1,4-dihydroxy-2-methylbenzene, 1,4-dihydroxy-2,3-dimethylbenzene, 1,4-dihydroxy-2,5-dimethylbenzene, 1,4-dihydroxy-2,6-dimethylbenzene, and 1,4-dihydroxy-2,3,5-trimethylbenzene, and the unsaturated compound is at least one member selected from the group consisting of acrylic acid, methyl acrylate, ethyl acrylate, acrylonitrile, acrylamide, acrolein, methacrylic acid, methyl methacrylate, ethyl methacrylate, isopropyl methacrylate, n-butyl methacrylate, isobutyl methacrylate, 2-hydroxyethyl methacrylate, 2-methylacrylonitrile, 2-methylacrylamide, methacrolein, crotonic acid, methyl crotonate, ethyl crotonate, crotononitrile, crotonamide, crotonaldehyde, crotonalcohol, 2-methylcrotonic acid, methyl 2-methylcrotonate, ethyl 2-methylcrotonate, 2-methylcrotononitrile, 2-methylcrotonamide, 2-methylcrotonaldehyde, 2-methylcrotonalcohol, 3-methylcrotonic acid, methyl 3-methylcrotonate, ethyl 3-methylcrotonate, 3-methylcrotononitrile, 3-methylcrotonamide, 3-methylcrotonaldehyde, 3-methylcrotonalcohol, 4-methyl-pent-4-enoic acid, 4-methyl-pent-4-enoic acid methyl ester, 4-methyl-pent-4-enoic acid ethyl ester, 4-methyl-pent-4-enal, 4-methyl-pent-4-en-1-ol, 3-methyl-but-3-en-1-ol, and 2-methyl-prop-2-en-1-ol.

4. A process for producing a chromancarboxylic acid ester represented by formula (4):
[F4]

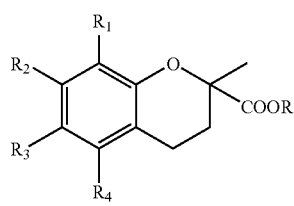

(4)

(wherein each of $R_1$ to $R_4$ represents a hydrogen atom, a halogen atom, a hydroxyl group, a methoxy group, an ethoxy group, a carboxyl group, or a C1 to C12 alkyl group which may have a substituent, a C6 to C12 aryl group which may have a substituent, a C7 to C12 aralkyl group which may have a substituent; $R_1$ to $R_4$ may be linked to one another; R represents a C1 to C12 alkyl group which may have a substituent, the substituent represents a halogen atom, a hydroxyl group, a carboxyl group or an ester group), characterized in that the process comprises allowing a phenol represented by formula (2):
[F5]

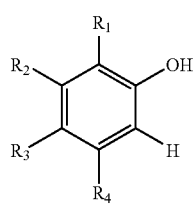

(2)

(wherein each of substituents $R_1$ to $R_4$ represents as same as those of formula (4)), a methacrylate ester represented by formula (5):
[F6]

(5)

(wherein R represents as same as that of formula (4)) and a formaldehyde to react in the absence of catalyst and in the presence of water in an amount by mole 1 to 10 times that of the phenol.

5. A process for producing a chromancarboxylic acid ester as described in claim 4, wherein the phenol is an alkylphenol or a polyhydroxybenzene.

6. A process for producing a chromancarboxylic acid ester as described in claim 5, wherein the phenol is at least one member selected from the group consisting of 2-methylphenol, 3-methylphenol, 4-methylphenol, 2,3-dimethylphenol, 2,4-dimethylphenol, 2,5-dimethylphenol, 3,4-dimethylphenol, 3,5-dimethylphenol, 2,3,4-trimethylphenol, 2,3,5-trimethylphenol, 2,4,5-trimethyl phenol, 3,4,5-trimethylphenol, 2,3,4,5-tetramethylphenol, hydroquinone, 1,4-dihydroxy-2-methylbenzene, 1,4-dihydroxy-2,3-dimethylbenzene, 1,4-dihydroxy-2,5-dimethylbenzene, 1,4-dihydroxy-2,6-dimethylbenzene, and 1,4-dihydroxy-2,3,5-trimethylbenzene, and the methacrylate ester is at least one member selected from the group consisting of methyl methacrylate, ethyl methacrylate, isopropyl methacrylate, n-butyl methacrylate, isobutyl methacrylate, and 2-hydroxyethyl methacrylate.

7. A process for producing a chromancarboxylic acid ester as described in claim 4, wherein the methacrylate ester and the formaldehyde are used in amounts in stoichiometrically excess of the amount of the phenol.

8. A process for producing a chromancarboxylic acid ester as described in claim 4, wherein the formaldehyde is at least one member selected from the group consisting of formaldehyde and paraformaldehyde.

9. A process for producing a chromancarboxylic acid, characterized by comprising hydrolyzing a chromancarboxylic acid ester produced through a process as recited in claim 4.

10. A process for producing methyl 6-hydroxy-2,5,7,8-tetramethylchroman-2-carboxylate, characterized in that the process comprises allowing 1,4-dihydroxy-2,3,5-trimethylbenzene, methyl methacrylate, and a formaldehyde to react in the absence of catalyst and in the presence of water in an amount by mole 1 to 10 times that of 1,4-dihydroxy-2,3,5-trimethylbenzene.

11. A process for producing a chromancarboxylic acid, characterized by comprising hydrolyzing methyl 6-hydroxy-2,5,7,8-tetramethylchroman-2-carboxylate produced through a process as recited in claim 10.

* * * * *